United States Patent [19]

Iguchi et al.

[11] Patent Number: 4,742,164

[45] Date of Patent: May 3, 1988

[54] BACTERIAL CELLULOSE-CONTAINING MOLDING MATERIAL HAVING HIGH DYNAMIC STRENGTH

[75] Inventors: Masatoshi Iguchi; Shigenobu Mitsuhashi, both of Sakuramura; Kunihiro Ichimura, Yatabemachi; Yoshio Nishi; Masaru Uryu, both of Tokyo; Shigeru Yamanaka, Yokohama; Kunihiko Watanabe, Kawasaki, all of Japan

[73] Assignees: Agency of Industrial Science and Technology; Sony Corporation; Ajinomoto Co., Inc., all of Tokyo, Japan

[21] Appl. No.: 852,838

[22] Filed: Apr. 16, 1986

[30] Foreign Application Priority Data

Apr. 16, 1985 [JP] Japan .................................. 60-79291
Jun. 7, 1985 [JP] Japan ................................ 60-122818

[51] Int. Cl.⁴ ........................... C08B 1/00; C08L 1/00
[52] U.S. Cl. ..................................... 536/56; 264/207; 435/823; 435/874; 106/163.1; 106/204

[58] Field of Search .................. 536/56; 435/823, 874; 264/207; 106/163.1, 204

[56] References Cited

U.S. PATENT DOCUMENTS

| 4,062,921 | 12/1977 | Austin | 264/207 |
| 4,320,198 | 3/1982 | Mynatt | 435/823 |
| 4,378,431 | 3/1983 | Brown | 435/823 |
| 4,474,949 | 10/1984 | Chatterjee et al. | 536/56 |

FOREIGN PATENT DOCUMENTS 2131701 6/1984 United Kingdom ............... 435/823

*Primary Examiner*—Ronald W. Griffin
*Attorney, Agent, or Firm*—Oblon, Fisher, Spivak, McClelland & Maier

[57] ABSTRACT

A molding material having high dynamic strength which contains bacterial cellulose having ribbon-shaped microfibrils.

Such material is advantageously used as a reinforcing material for composite plastics having high strength, as high quality paper or as acoustic diaphragms for percussion instruments.

26 Claims, 3 Drawing Sheets

BACTERIAL CELLULOSE-CONTAINING MOLDING MATERIAL HAVING HIGH DYNAMIC STRENGTH

BACKGROUND OF THE INVENTION

1. Field of the Invention

The present invention relates to a molding material having high dynamic strength which entails ribbon-like microfibrils of bacterial cellulose.

2. Description of the Background

Bacterial cellulose has been used in the production of medical pads. In particular, such pads utilize the sheet-like cellulose produced by *Acetobacter xylinum* ATCC 23769. See Japanese Published Examined patent application No. 120159/84.

On the other hand, various materials are known as conventional molding materials. For example, it is known that cellulose, cellophane, and celluloid, obtained by dissolving cellulose derivatives and then finishing the same, are known, as well as fibers for thread-like, sheet-like or various solid moldings. Various synthetic high molecular weight materials have also been developed and include those having improved dynamic strength by the orientation of molecular chains in a definite direction.

The dynamic strength of conventional cellulose and cellulose derivatives derived from various plants is not very great. For example, the modulus of elasticity of celluloid or cellophane in sheet form is approximately 2 to 3 GPa at the maximum.

Moreover, synthetic high molecular weight materials obtained by orienting the molecular chains in a definite direction have been found to have limited utility due to the poor modulus of elasticity in the other directions. For this reason, materials having no anisotropy in molecular orientation but having excellent strength as structural materials have been desired. However, high molecular weight materials in which molecules are arranged at random exhibit a poor modulus of elasticity. As molding materials of synthetic high molecular weight having high efficiency, polyester films, aramid sheets, polyimide films and the like are known, but the module of elasticity of the same are approximately 4 to 7 GPa.

Thus, at present, bacterial cellulose has been used only in the preparation of medical pads. Such material has never been used, nor is anything known about the use of the same, in the preparation of items having high dynamic strength.

Nevertheless, a need clearly continues to exist for a molding material which has both excellent elasticity and high tensile or dynamic strength.

SUMMARY OF THE INVENTION

Accordingly, it is an object of the present invention to provide a highly elastic molding material which has excellent tensile strength.

It is also an object of the present invention to provide a molding material having excellent hydrophilic properties and having low toxicity.

It is, further, an object of this invention to provide a molding material having excellent electrical and thermal conductivity, as well as excellent resistance to chemical attack and weathering.

Moreover, it is also an object of this invention to provide a molding material having excellent magnetic and insulating properties.

According to the present invention, the foregoing and other objects are attained by providing a molding material having high dynamic strength which contains bacterial cellulose containing ribbon-like cellulose microfibrils.

DETAILED DESCRIPTION OF THE PREFERRED EMBODIMENTS

Figure 1:
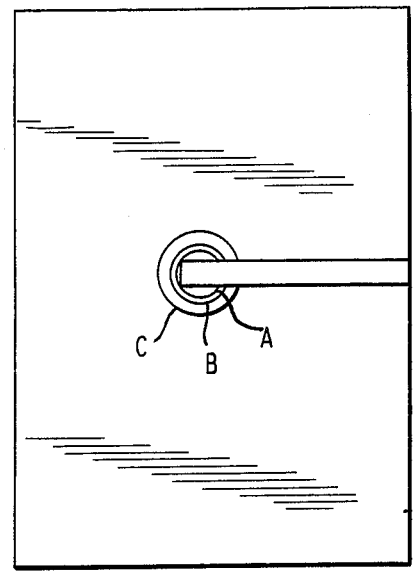
FIGS. 1 and 2 show X-ray diffraction patterns of the products of the present invention.

The present invention relates to highly elastic and highly strong molding materials having excellent tensile strength and stretch resistance which are obtained by incorporating therein a specific cellulose produced by bacteria. The molding materials can be utilized not only as paper and as other various sheets but also as thread-like or various solid moldings.

According to the present invention, it has now been found that cellulose entailing ribbon-like or shaped microfibrils produced by microorganisms has an extremely large dynamic strength, such as a tensile strength. Moreover, the foregoing objects can be achieved by using as molding materials materials having incorporated therein this bacteria cellulose. The present invention in all aspects thereof is predicated upon this surprising discovery.

As noted, the present invention relates to molding materials having a high dynamic strength which contains bacterial cellulose containing ribbon-like or ribbon-shaped microfibrils.

The bacterial cellulose entails ribbon-like microfibrils of approximately 100 to 500 Å in width and approximately 10 to 200 Å in thickness, i.e., by electron microscopic observation.

This cellulose is readily decomposed by cellulose to form glucose. Namely, cellulase (EC 3.2.1.4) (manufactured by Amano Pharmaceutical Co., Ltd.) was dissolved in a 0.1% (w/v) suspension of this cellulose in an amount of 0.5% (w/v) and the mixture was reacted at 30° C. for 24 hours in a 0.1M acetate buffer. As a result, it was observed that a part of this substance was decomposed. The supernatant was developed by paper chromatography, whereby cello-oligosaccharides and glucose were detected. In addition, a small quantity of hexose other than glucose was detected.

Namely, the bacterial cellulose of the present invention contains cellulose and hetero polysaccharides having cellulose as a main chain and which contain $\beta$-1,2-, $\beta$-1,3- etc. glucans. In the case of hetero polysaccharides, constituent components other than cellulose are hexose, pentose and organic acids such as mannose, fructose, galactose, xylose, arabinose, ramnose, glucuronic acid, etc. These polysaccharides may be single substances, alternatively, two or more polysaccharides may be mixed via hydrogen bonding.

Any bacterial cellulose is usable as the bacterial cellulose described above.

Microorganisms that produce such bacterial cellulose are not particularly limited, but *Acetobacter aceti subsp. xylinum* ATCC 10821, *Acetobacter pasteurianus, Acetobacter rancens, Sarcina ventriculi, Bacterium xylineide*, and bacteria belonging to the genus Pseudomonas, the genus Agrobacterium, etc. which produce bacterial cellulose can be utilized.

A method for culturing these microorganisms and accumulating bacterial cellulose may be in a conventional manner for culturing bacteria. That is, microorganisms are inoculated on conventional nutrient media containing carbon sources, nitrogen sources, inorganic salts and, if necessary, organic trace nutrients such as amino acids, vitamins, etc. followed by settling or gentle aerial shaking. As carbon sources, glucose, sucrose, maltose, starch hydrolysates, molasses, etc. are utilized but ethanol, acetic acid, citric acid, etc. may also be utilized singly or in combination with the above-described sugar. As nitrogen sources, organic or inorganic nitrogen sources such as ammonium salts, e.g., ammonium sulfate, ammonium chloride, ammonium phosphate, etc., nitrates, urea, peptone or the like are utilized. Inorganic salts, phosphates, magnesium salts, calcium salts, iron salts, manganese salts, etc. are utilized. As organic trace nutrients, amino acids, vitamins, fatty acids, nucleic acids and further peptone, casamino acid, yeast extracts, soybean protein hydrolysates, etc. containing these nutrients are utilized. When using auxotrophs requiring amino acids, etc. for growth, it is necessary to further supplement the required nutrients.

Culture conditions may be conventional; while controlling pH to about 9 and the temperature to about 20° to 40° C., culture is performed for 1 to 30 days and bacterial cellulose is accumulated on the surface layer in a gel form.

The gel is withdrawn and washed with water, if necessary. Depending upon the intended purpose, the washing water may be supplemented with chemicals such as sterilizers and pre-treating agents, for example.

After washing with water, the gel is dried or kneaded with other materials to be kneaded, etc. to provide for use.

It is preferred that the bacterial cellulose be of such a structure in which the microfibril is intertwined, in order to enhance the dynamic strength, such as tensile strength, etc. For this reason, for example, a method which entails pressing the gel withdrawn from the culture from the orthogonal direction, squeezing most of the free water off and then drying is effective. It is appropriate that the squeezing pressure be approximately under 1 to 10 kg/cm$^2$. By this press squeezing, the cellulose after drying is oriented along the press squeezing direction. Further, by stretching to one direction while applying pressure, i.e., by performing a rolling operation, the cellulose after drying comes to be oriented also to the rolling direction, in addition to the press squeezing direction. Pressing apparatuses can be appropriately chosen and utilized from commercially available machines.

On the other hand, it is also effective to macerate the bacterial cellulose once, in order to increase the dynamic strength. Maceration may be carried out by utilizing mechanical shearing force, and the bacterial cellulose can easily be macerated with, for example, a rotary macerator, or a mixer, etc. It is also effective to conduct the aforesaid press squeezing after maceration.

The present molding material having a high dynamic strength can be molded into various shapes such as sheet-like, yarn-like, cloth-like, solid-like shapes, for example.

When molding into a sheet-like form, the bacterial cellulose is, if necessary, macerated and then formed into a layer shape, which is squeezed under pressure, if necessary, and then dried. By press squeezing, a planar-oriented sheet is obtained; by further rolling, a sheet which is not only planar-oriented but also uniaxially oriented can be obtained.

It is preferable that the drying of the sheet which is macerated and/or press squeezed be carried out by fixing on a suitable support. By fixing on the support, a degree of planar orientation is further enhanced and, a sheet having a large dynamic strength can be obtained. As supports, a plate, a glass plate, a metal plate, etc. having, e.g., a net structure, can be utilized. Any drying temperature can be used as long as the temperature is within a range where the cellulose is not decomposed. In addition to a heat drying method, a freeze drying method can also be utilized.

The thus obtained sheet takes a structure in which the microfibril is intertwined at random. According to X-ray diffraction patterns, the press-squeezed sheet has a planar orientation; the additionally rolled sheet also has a planar orientation and at the same time, a uniaxial orientation. The modulus of elasticity of the sheet is generally about 10 to 20 GPa.

The thickness of the sheet can be determined depending upon the utility but is generally about 1 to 500 μm.

The sheet may also contain various additives. For example, by incorporating solutions (aqueous or non-aqueous), emulsions, dispersions, powders, melts, etc. of various high molecular weight materials, having variable properties such as high strength, resistance to water, chemicals and weathering, water repellency, antistatic property, etc., such properties can be imparted to the sheet, depending upon the properties of the additives. By incorporating metals such as aluminum, copper, iron, zinc, etc. or carbon in a powdery form or yarn form, electroconductivity and thermal conductivity can be increased. Further by incorporating inorganic materials such as titanium oxide, iron oxides, calcium carbonate, kaolin, bentonite, zeolite, mica, alumina, etc., heat resistance, and insulating properties can be improved or even smoothness can be imparted to the surface, depending upon kind thereof. By incorporating lower molecular weight organic materials or adhesives, the strength can be further increased. The sheet may also be colored with coloring agents such as phthalocyanine, azo compounds, indigos, safflowers, etc. For coloration, various paints, dyes and pigments can be used in addition thereto. By incorporating medicines or sterilizers, the sheet can also be utilized as a medical sheet.

These kneadings and additives are incorporated in an appropriate range not exceeding 97% but in an amount sufficient to impart the desired physical property. The time for incorporation is not limited but incorporation may occur in the bacterial cellulose gel or a maceration product thereof; alternatively, it may occur after press squeezing or after drying. Further, they may be incorporated in media or cultures in some occasions. A method of the incorporation may be by impregnation, in addition to mixing.

On such a sheet can also be laminated a layer of other materials. The laminate can be appropriately chosen depending upon purpose of sheet to be used. The laminate can also be chosen from the aforesaid kneadings or additives; for example, various high molecular weight materials can be coated to impart a waterproofed character.

In the case of making paper, the bacterial cellulose is macerated, then subjected to paper making and then drying, whereby paper having excellent tensile strength, resistance to expansion, etc. and at the same time, having high elasticity and high strength which is chemically stable and excellent in water absorbancy and air permeability can be obtained. In this case, conventional additives, treating agents, etc. used for paper making can be utilized and kneadings and additives can also be appropriately chosen from the aforesaid substances and incorporated in the paper.

In recent years, the demand for electrically insulating paper, heat resistant paper, and fire retarding paper, for example, has increased and synthetic paper, inorganic paper, etc. using noncellulose fibers have been prepared. When wet methods are used to prepare such paper, it is necessary to prepare the paper by incorporating cellulose pulp therein, because non-cellulose fibers fail to form any hydrogen bond, except for the case where pulp fibers such as fibers of polyethylene, polypropylene, polyacrylonitrile, and aromatic polyamide, etc. are used. In this case, it is necessary that the amount of pulp be minimized as much as possible to enhance the insulating, heat resistant and fire retarding properties. When mixing conventional wood pulp with paper, however, the added amount reaches 20 to 50% and the purpose cannot be sufficiently achieved. To the contrary, the amount of cellulose can be greatly reduced by the use of bacterial cellulose instead of wood pulp and, paper having excellent insulating, heat resistant and fire retarding properties can be obtained. Accordingly, the molding material having a high dynamic strength of the present invention is also effective for each purpose.

Further, it has been observed that photo-cross linked polyvinyl alcohol has a good affinity to the living tissues as compared to conventional photo-cross linked resins and it is believed that the utility of immobilized agents for enzymes, microorganisms, etc. could be so further improved. Photoresists used for making original printing plates are prepared by coating a resin on a base plate, projecting a design, etc. to be printed thereon to cause photo-cross linking and then hardening the resin, and washing the unhardened resin off. The photo-cross linkable polyvinyl alcohol which is water-soluble has advantages in that it is inexpensive and washing thereof is easy compared to conventional oil-soluble resins and is, moreover, expected to have application also to photoresists. In these cases, however, there is a problem that photocross linkable polyvinyl alcohol swells with water and the cross linking structure is destroyed. However, this swelling can be prevented by incorporating the bacterial cellulose.

In the case of yarn, for example, the bacterial cellulose gel or macerated product thereof is washed, dried and then dissolved in a dimethylacetamide/lithium chloride solvent, etc. The solution is spun using a coagulating solution such as water, alcohols, ketones, dioxane, tetrahydrofuran, etc. in which cellulose is insoluble and the solvent for the cellulose is miscible.

In the case of cloth, this yarn is used and woven in a conventional manner.

In the case of a solid structure, various plastics are kneaded with or laminated on the bacterial cellulose to form the desired molding. This molding is usable in place of, e.g., various FRP products or carbon fiber products.

The present bacterial cellulose, as noted, entails a ribbon-like microfibril and provides a large dynamic strength such as a tensile strength, as well as excellent expansion resistance and elasticity, etc. Moreover, the dynamic strength is enhanced by the microfibrils being intertwined; and by imparting an orientation thereto, the strength to such a direction is further increased. The bacterial cellulose has a property that is readily oriented by pressing.

The present invention will now be further illustrated by certain examples and references which are provided for purposes of illustration only and are not intended to limit the present invention.

EXAMPLE 1

An Erlenmeyer flask of 200 ml volume was charged with 50 ml of a medium having a composition of 5 g/dl of sucrose, 0.5 g/dl of yeast extract (Difco), 0.3 g/dl of $KH_2PO_4$ and 0.05 g/dl of $MgSO_4.7H_2O$ (pH 5.0) followed by sterilizing with steam at 120° C. for 20 minutes. A platinum loop of *Acetobacter aceti subsp. xylinum* ATCC 10821 grown (30° C., 30 days) in a test tube slant agar medium (pH 6.0) having a composition of 0.5 g/dl of yeast extract, 0.3 g/dl of peptone and 2.5 g/dl of mannitol (pH 6.0) was inoculated on the sterilized medium followed by culturing at 30° C. Thirty days after, a gel-like membrane containing white bacterial cellulosic polysaccharides was formed on the surface layer of the culture solution.

The thus obtained gel-like membrane was washed with water and spread in a thickness of about 1 cm. By pressing the membrane under a pressure of about 10 kg/cm$^2$ using a test pressing machine (Tester Industry Co., Ltd.), water was squeezed off. This was attached to a glass plate and dried at 105° C. for 2 hours to obtain a sheet having a thickness of about 10 μm.

An X-ray diffraction pattern of the thus obtained sheet is shown in FIG. 1. This figure indicates a diffraction pattern obtained by taking its rotation axis parallel to the sheet plane and photographing with X-rays incident upon the direction orthogonal to the rotation axis. As shown in the figure, (a) plane 101, (b) plane 10$\bar{1}$ and (c) plane 002 are all oriented and this sheet undergoes planar orientation to an extremely high degree.

With respect to this sheet, a known cellulosic sheet and various high molecular weight secondary materials are tested for module of elasticity using a tensile tester for purposes of comparison. The results are shown in Table 1.

TABLE 1

| Sheet | Modulus of Elasticity |
| --- | --- |
| This invention | 15.8 GPa |
| Cellophane | 1.5 |
| Celluloid | 2.0 |
| Nomex*[1] | 7.0 |
| Lumilar*[2] | 4.9 |

*[1]Sheet of polymetaphenylene isophthalamide
*[2]Sheet of biaxially oriented polyethylene terephthalate

EXAMPLE 2

Gel-like bacterial cellulose as used in Example 1 was squeezed under pressure while rolling it in one direction using a roll pressing machine (Yoshida Kogyo K.K.). The squeezed cellulose was attached to a glass plate likewise and dried at 105° C. for 2 hours to obtain a sheet.

Figure 2:
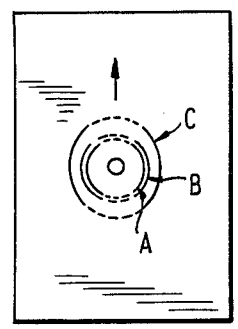

An X-ray diffraction pattern of the thus obtained sheet is shown in FIG. 2. This figure indicates a diffraction pattern obtained by fixing the sheet and photographing with X-rays incident upon the direction perpendicular to the film surface. In the figure, the symbol arrow indicates the rolling direction. As shown in the figure, orientation is found in all of (a) plane 101, (b) plane 101 and (c) plane 002 and uniaxial orientation is noted. Further, with respect to planar orientation, an orientation almost similar to that of FIG. 1 was noted.

The modulus of elasticity of this sheet was measured in a manner similar to Example 1 and showed 20 GPa in the rolling direction.

EXAMPLE 3

The bacterial cellulose was incorporated in novoloid fibers (manufactured by Gun-Ei Chemical Industry Co., Ltd., trademark, Kainol Fiber KP 0203, $\phi$14 $\mu$m, 3 mm in length) and a sheet having a weight of 60 g/m² was subjected to paper making according to the TAPPI method (TAPPI standard T 205 m-58).

Further for the purpose of comparison, papier mache of ordinary wood pulp (N.U.SP) beaten to a high degree (CSF 245 ml) and Kainol Fiber was also prepared.

The breaking length of each of these sheets was measured using an automatic recording tensile tester. The results are shown in Table 2.

TABLE 2

| | | | | Breaking Length |
|---|---|---|---|---|
| Kainol | 95 parts | B.C.* | 5 parts | 0.33 km |
| Kainol | 90 parts | B.C.* | 10 parts | 0.79 km |
| Kainol | 80 parts | B.C.* | 20 parts | 1.67 km |
| Kainol | 90 parts | N.U.SP | 10 parts | 0.12 km |

*B.C.: bacterial cellulose

By the use of the bacterial cellulose, paper making is enabled and the strength was increased, by the incorporation in a small amount. In the case of using conventional pulp, paper making was impossible by the use of less than 10 parts.

EXAMPLE 4

Using various inorganic fibers, papier mache with the bacterial cellulose was prepared and each breaking length was measured. The results are shown in Table 3.

TABLE 3

| Carbon fiber (Toray, Toreka T 008) 3 mm long | 95 parts | Breaking length | 0.15 km |
|---|---|---|---|
| Bacterial cellulose | 5 parts | | |
| Carbon fiber (Toray, Toreka T 008) 6 mm long | 90 parts | Breaking length | 0.64 km |
| Bacterial cellulose | 5 parts | | |
| Alumina fiber (made by Denka, Arecen Bulk) | 90 parts | Breaking length | 0.24 km |
| Bacterial cellulose | 5 parts | | |

In any case, paper making was enabled by the incorporation of 5 to 10%.

EXAMPLE 5

Gel-like bacterial cellulose was pressed and dried to obtain a sheet. Young's modulus E of the sheet measured by the oscillation lead method was as follows.

E=13.6 GPa

This value is 5 to 10 times Young's modulus of conventional paper prepared from wood pulp alone.

EXAMPLE 6

Gel-like bacterial cellulose was macerated with a homogenizer followed by paper making according to the TAPPI method. Young's modulus E of the sheet measured by the oscillation lead method was:

E=7.4 GPa

Further, for purposes of improving freeness and yield of fine particles, 5% (solid content ratio) of polyamide epichlorohydrin resin (manufactured by Dick Hercules Co., Ltd., Kaimen 557H) was incorporated therein followed by paper making. E of this paper was as follows:

E=8.1 GPa

In any case, paper having a high strength was obtained.

EXAMPLE 7

To bacterial cellulose was added wood pulp (N.U.KP) (CSF, 540 ml). Further, 5% (solid content ratio) of aluminum sulfate was added to the mixture followed by paper making. Properties of paper thus obtained were as follows:

| N.U.KP | 100 parts | Breaking length | 3.69 km |
|---|---|---|---|
| N.U.KP B.C. | 80 parts 20 parts | Breaking length | 4.81 km |
| N.U.KP | 100 parts | E = 1.38 GPa | |
| N.U.KP B.C. | 80 parts 20 parts | E = 2.16 GPa | |

By the addition of the bacterial cellulose, the strength of paper was improved.

EXAMPLE 8

After macerating gel-like bacterial cellulose obtained by definite culture with a standard pulp macerator, it was filtered using a sieve of 125 mesh to obtain about 8.8% in a solid content of the maceration paste. The paste was used in the following experiments.

Photo-cross linkable polyvinyl alcohol (PVA)-SbQ (GH-17SbQ, 10.5 wt%, 1.2 mol%, manufactured by Toyo Gosei Kyogyo K.K.), the maceration paste described above and water were mixed in a dark room in ratios shown in Table 4.

TABLE 4

| Sample | (a) | (b) | (c) |
|---|---|---|---|
| 1 | 21.0 | 6.0 | 7.5 |
| 2 | 21.0 | 1.8 | 11.7 |
| 3 | 21.0 | 0.6 | 12.9 |
| 4 | 21.0 | 0 | 13.5 |

(a) PVA-SbQ (GH 17 SbQ, 10.5 wt %, 1.2 mol %)
(b) macerated bacteria cellulose (calculated as dry weight)
(c) $H_2O$ Each mixture shown in the table above was spread over an acryl plate in a thickness of about 0.7 mm using a glass rod. After air drying overnight, it was further air dried at 40° C. for 30 minutes. These operations were performed in the dark room. The system was exposed to sunlight for 30 minutes to cause cross-linking. Thus, a sheet was obtained.

The sheet was cut into a ribbon-like shape of 3×1 cm and put in water to conduct a swelling test for 2 hours. The results are shown in Table 5.

TABLE 5

| Sample | Length × Width (cm) 0 h → 2 h | | Swelling Rate of Length | Weight × $10^2$ (g) 0 h → 2 h | | Swelling Rate of Weight |
|---|---|---|---|---|---|---|
| 1 | 3 × 1 | 3.2 × 1.1 | 1.07 | 2.46 | 4.87 | 1.98 |
| 2 | 3 × 1 | 3.3 × 1.1 | 1.10 | 1.18 | 2.56 | 2.17 |
| 3 | 3 × 1 | 3.3 × 1.1 | 1.10 | 1.43 | 3.34 | 2.36 |
| 4 | 3 × 1 | 4.0 × 1.3 | 1.33 | 1.02 | 2.63 | 2.50 |

By incorporating the bacteria cellulose, swelling could be prevented.

Next, a tensile test of the sheet was performed. The results are shown in Table 6.

TABLE 6

| Sample | Modulus of Tensile Elasticity (GPa) |
|---|---|
| 1 | 1.61 |
| 2 | 1.71 |
| 3 | 1.32 |
| 4 | 1.01 |

By incorporating the bacteria cellulose, the modulus of elasticity could be improved to 1.3 to 1.6 times.

EXAMPLE 9

Each mixture of the compositions shown in Example 8 was sandwiched between two glass plates using as a spacer a slide glass having a thickness of 1 mm. The system was exposed to sunlight for 30 minutes as is to cause cross linking and a gel similar to konjak in a wet state was obtained. The gel was put in distilled water and the swelling test was performed in a manner similar to Example 8. The results are shown in Table 7.

TABLE 7

| Sample | Weight (g) 0 h | → 2 h | Ratio of Water Absorbancy |
|---|---|---|---|
| 1 | 1.75 | 3.97 | 2.3 |
| 2 | 0.90 | 3.95 | 4.4 |
| 3 | 0.48 | 5.05 | 10.05* |
| 4 | 1.74 | 40.3 | 23.2* |

*Samples 3 and 4 were destroyed by swelling.

By incorporating the bacterial cellulose, swelling and destruction of the gel were prevented.

EXAMPLE 10

To 3.5 parts of dry bacterial cellulose were added 100 parts of dimethylacetamide. The mixture was refluxed with stirring for 60 minutes. Next, the mixture was cooled to 100° C. After slowly adding 10 parts of lithium chloride, the mixture was stirred at room temperature overnight to dissolve the bacterial cellulose. This spinning dope was spun in a tetrahydrofuran coagulating solution in a spinning draft of 1.5 and a bath length of 80 cm. Yarns coming from a spinning bath were 50% stretched in water (50° C.) and then dried. Properties of the fibers obtained are shown in Table 8. For purpose of comparison, wood pulp (L.B. KP) was spun in a similar manner.

TABLE 8

| | Dry Strength (g/d) | Wet Strength (g/d) | Dry Stretching (%) | Wet Stretching (%) |
|---|---|---|---|---|
| BC | 5.4 | 4.6 | 8.1 | 12.3 |
| L.B.KP | 3.2 | 2.1 | 5.7 | 7.9 |

EXAMPLE 11

To a mixture of copper powders (manufactured by Fukuda Kinzokuhakufun Kogyo K.K., $\phi 10$ $\mu$m) and wood pulp (N.U. KP) (CSF. 540 ml) macerated bacterial cellulose was added and the mixture was subjected to paper making by the TAPPI method. Further, for purpose of comparison, papier mache of copper powders and wood pulp was also prepared. With respect to these sheets, physical properties were measured using an automatic recording tensile tester. The results are shown in Table 9.

TABLE 9

| | | Stretching (%) | Strength (kg/mm$^2$) | Modulus of Elasticity (kg/mm$^2$) |
|---|---|---|---|---|
| Copper powders | 100 parts | 1.6 | 0.68 | 56 |
| N.U.KP | 10 parts | | | |
| BC | 5 parts | | | |
| Copper powders | 100 parts | | | |
| N.U.KP | 10 parts | 1.6 | 0.23 | 31 |

By use of the bacterial cellulose, the copper powders did not leak and the strength was greatly improved. In the case of conventional pulp, more than 60% of the copper powders leaked.

EXAMPLE 12

To wood pulp (N.U.KP) (CSF, 540 ml) was added macerated bacteria cellulose (BC) followed by paper making by the TAPPI method. This paper was impregnated with phenol resin and air dried. By hot press finishing, a phenol laminate plate was prepared. Further, for purposes of comparison, a phenol laminate plate comprising wood pulp alone was also prepared in a similar manner. These phenol laminate plates were molded into dumbbell moldel No. 1 JIS K-7113) and physical properties were measured using an automatic recording tensile tester. The results are shown in Table 10.

TABLE 10

| | | Stretching (%) | Strength (kg/cm$^2$) | Modulus of Elasticity (kg/mm$^2$) |
|---|---|---|---|---|
| N.U.KP | 95 parts | | | |
| BC | 5 parts | 5.2 | 808 | 4400 |
| N.U.KP | 100 parts | 4.4 | 658 | 3300 |

By the use of the bacterial cellulose, the strength of the phenol laminate plate was greatly improved.

EXAMPLE 13

Gel-like bacterial cellulose as used in Example 1 was subjected to hot pressing (Yoshida Kogyo K.K.) at 150° C. under 5 kg/cm$^2$ for 5 minutes to obtain a sheet. A polyethyleneimine-treated polyethylene film was laminated onto the thus obtained sheet at 320° C. to prepare a laminate film. With respect to the laminate film, physical properties were measured using an automatic recording tensile tester. As a result, the laminate film having a greatly improved modulus of elasticity of 16.2 GPa was obtained as compared to an ordinary cellophane-polyethylene laminate film showing a modulus of elasticity of 1.7 GPa.

EXAMPLE 14

To silicon nitride and silicon carbide (manufactured by Tateho Chemical Co., Ltd., 10 μm in length) was added macerated bacterial cellulose (BC) followed by paper making by the TAPPI method. Further for comparison, papier mache of wood pulp (N.U.KP) and microfibril cellulose (MFC, manufactured by Daicel Chemical Co., Ltd.) were also treated in a similar manner. With respect to the sheets obtained, physical properties were measured using an automatic recording tensile tester. The results are shown in Table 11.

TABLE 11

|  | Modulus of Elasticity (kg/mm$^2$) |
|---|---|
| Silicon nitride, 100 parts, BC, 5 parts | 15 |
| Silicon nitride, 100 parts, BC, 3 parts | 12 |
| Silicon nitride, 100 parts, BC, 10 parts | 36 |
| Silicon nitride, 100 parts, N.U.KP, 5 parts | 8 |

By use of the bacteria cellulose, no leakage of silicon nitride and silicon carbide occurred but the modulus of elasticity was greatly improved. In the case of ordinary pulp, 60% or more of silicon nitride and silicon carbide leaked out. In the case of MFC, most of the silicon nitride and carbide leaked out.

EXAMPLE 15

A Sakaguchi flask of a 500 ml volume was charged with a 50 ml aliquot of liquid medium having a composition of 2 g/dl of fumaric acid, 0.2 g/dl of dihydrogen potassium phosphate, 1 mg/dl of magnesium sulfate tetrahydrate, 1 mg/dl of magnesium sulfate heptahydrate, 0.05 g/dl of calcium chloride, 1.0 g/dl of yeast extract (Difco) and 1.0 g/dl of peptone (Difco) adjusted pH to 7.0 using ammonia, and one platinum loop each of *E. coli* ATCC 11775 was inoculated on the medium followed by culturing at 30° C. for 24 hours. Then, bacteria were recovered by centrifugation in a conventional manner. After washing with physiological saline twice, the bacteria were suspended in the same amount of physiological saline as its wet weight.

By the following method, an attempt was made to immobilize the bacteria to a carrier prepared from gelatin and the cellulose. As the method for immobilization, a method for immobilization using transglutaminase described in Published Unexamined Japanese Patent Application No. 66886/84 was used. Gelatin (Miyagi-Kagaku) and the cellulosic substance macerated were mixed in ratios shown in Table 12. To this mixture, the bacteria were further added in a concentration of 3.5% and, the mixture was gelled in the manner described in Published Unexamined Japanese Patent Application No. 66886/84. That is, 0.1 unit was added per 1 mg of transglutaminase. The mixture was allowed to stand at 25° C. for 1 hour to cause gelation. The gel was diced into 5 mm squares and added to the reaction mixture to examine the activity of apartase. The reaction mixture contained 20 g/dl of fumaric acid and 1 mM of MgSO$_4$.7H$_2$O and the pH was adjusted to 8.5 using ammonia. Bacterial-immobilized gelatin gel was added to the reaction mixture in a bacterial concentration of 0.5% based on the total amount of the reaction mixture. The reaction was carried out for 1 hour. Every 5 minutes the concentration of aspartic acid was quantitatively assayed by ninhydrin colorimetry to determine the initial reaction rate. The count of the bacteria leaked into the reaction mixture was determined by colony count after 30 minutes lapsed from the initiation of the reaction. The results are shown in Table 12.

TABLE 12

| Concentration of Gelatin (%) | Reinforcement and Addition | Amount (%) | Count of Bacteria Leaked (cella/ml) |
|---|---|---|---|
| 12.5 |  | 0 | $1.2 \times 10^8$ |
| 12.0 | macerated bacterial cellulose | 0.5 | $1.1 \times 10^7$ |
| 12.5 |  | 0.5 | $9.8 \times 10^4$ |
| 12.0 | polyester gauze | 0.5 | $1.4 \times 10^8$ |
| 12.5 |  | 0.5 | $1.1 \times 10^8$ |

The enzyme activity was determined from the initial reaction rate. The enzyme activity was expressed by a relative value, designating 100 as a first instance when adding no cellulosic substance. Further, the reaction was repeated 10 times. The results are shown in Table 13.

TABLE 13

| Concentration of Gelatin (%) | Reinforcement and Addition | Amount (%) | Relative Activity of Aspartase 1st | Relative Activity of Aspartase 10th |
|---|---|---|---|---|
| 12.5 |  | 0 | 100 | 35 |
| 12.0 | present cellulosic substance | 0.5 | 99 | 80 |
| 12.5 |  | 0.5 | 102 | 85 |
| 12.0 | polyester gauze | 0.5 | 103 | 37 |
| 12.5 |  | 0.5 | 97 | 38 |

By incorporating the cellulosic substance, leakage of the bacteria was prevented so that it became possible to maintain the activity after repeated use.

Further, the breaking strength of gel supplemented with gelatin and the reinforcing material similar to those shown in Table 12 was measured. The measurement was performed by expressing as a breaking strength the maximum load obtained by causing gelation of the aforesaid gelatin solution in a cylindrical plastic container having a diameter of 22 cm, then setting it in a rheometer (Fudo Kogyo K.K., NRM 2002 J) and immersing an adapter of 5 mmφ directly into the gel. The results are shown in Table 14.

TABLE 14

| Concentration of Gelatin (%) | Reinforcement and Addition | Amount (%) | Breaking Strength (%) |
|---|---|---|---|
| 12.5 |  | 0 | 90 |
| 12.5 | present cellulosic substance | 0.5 | 145 |
| 12.5 |  | 0.5 | 194 |
| 12.0 | polyester gauze | 0.5 | 111 |
| 12.5 |  | 0.5 | 128 |

With the cellulosic material, a reinforcing effect superior to that of conventional reinforcement was noted.

EXAMPLE 16

Immobilization to alginic acid gel was conducted by mixing sodium alginate with the cellulosic substance according to Table 15. Thereafter, the mixture was dropwise added to a 0.1M CaCl$_2$ solution to obtain a bead-like gel.

The apartase reaction was carried out under the same reaction conditions as used in Example 15. The count of bacteria leaked was determined by the number of colony 30 minutes after without exchanging the reaction mixture. The results are shown in Table 15.

TABLE 15

| Concentration of Alginic Acid (%) | Reinforcement and Addition | Amount (%) | Count of Bacteria Leaked 30 Minutes after (cells/ml) |
|---|---|---|---|
| 1.5 |  | 0 | 2.1 × 10$^8$ |
| 1.0 | present cellulosic substance | 0.5 | 5.3 × 10$^6$ |
| 1.5 |  | 0.5 | 1.5 × 10$^5$ |
| 1.0 | polyester gauze | 0.5 | 1.9 × 10$^8$ |
| 1.5 |  | 0.5 | 2.0 × 10$^8$ |

The reaction solution described above was replenished every 15 minutes and the reaction of the immobilized carrier was carried out 4 times in total. The enzyme activity was determined from its initial rate by measuring the concentration of aspartic acid every 3 minutes. The results are shown in Table 16. The apartase activity is shown by a relative values, designating 100 as the case when adding no cellulosic substance. The results are shown in Table 16.

TABLE 16

| Concentration of Aspartic Acid (%) | Reinforcement and Addition | Amount (%) | Relative Activity of Aspartase | | | | |
|---|---|---|---|---|---|---|---|
| 1.5 |  | 0 | 100 | 85 | 32 | 20 | |
| 1.0 | present cellulosic substance | 0.5 | 101 | 92 | 79 | 60 | |
| 1.5 | present cellulosic substance | 0.5 | 97 | 90 | 87 | 85 | |
| 1.0 | polyester gauze | 0.5 | 101 | 80 | 29 | 19 | |
| 1.5 | polyester gauze | 0.5 | 98 | 89 | 39 | 25 | |

As a result of supplementing the cellulosic substance as a reinforcement, leakage of the bacteria was prevented so that it became possible to repeatedly use the immobilized carrier having a high strength of the wood pulp, as compared to a conventional immobilized carrier.

EXAMPLE 17

In the following manner, invertase was immobilized onto a photo-cross linkable resin. A mixture of 1 part of invertase and 2 parts of phosphate buffer (pH 6.0) was mixed with 20 parts of a photo-cross linkable resin solution (pH 6.0). The mixture was spread over a glass plate. After air drying for 1 day, irradiation with light was performed for 1 hour to cause cross linking and hardening. The reinforcement was incorporated in a final concentration of 5%.

The immobilized membrane was cut into a size of 5×5 mm and reacted in 50 ml of a solution of 4 g of sucrose at 40° C. for 24 hours with stirring to examine the decomposition rate of sucrose. The reaction was repeated 10 times. Further, the breaking stress and modulus of elasticity were also examined. The results are shown in Table 17.

TABLE 17

| Reinforcement and Addition Amount (%) | | Breaking Stress (MPa) | Modulus of Elasticity (GPa) | Relative Activity of Invertase | |
|---|---|---|---|---|---|
| | | | | 1st | 10th |
| | 0 | 25.1 | 0.95 | 100 | 98 |
| Present cellulosic substance | 5 | 32.0 | 1.53 | 100 | 99 |
| Polyester gauze | 5 | 28.3 | 1.20 | 100 | 98 |

By incorporating the cellulosic substance, physical properties of the membrane such as the breaking shear, modulus of elasticity etc., of the membrane representing the strength of the immobilized enzyme membrane were greatly improved. For this reason, operations for immobilization of enzyme become easy and the time period required for the operations in the case of incorporating the cellulosic substance is shortened to about ¾ for the case in which no cellulosic substance was incorporated.

EXAMPLE 18

Preparation of bacterial cellulose:

An Erlenmeyer flask of a 200 ml volume was charged with 50 ml of medium (pH 5.0) having a composition of 5 g/dl of sucrose, 0.5 g/dl of yeast extraction, 0.5 g/dl of ammonium sulfate, 0.3 g/dl of hydrogen potassium phosphate (KH$_2$PO$_4$) and 0.05 g/dl of magnesium sulfate (MgSO$_4$.7H$_2$O) followed by sterilization with steam at 120° C. for 20 minutes. Thus a culture solution was prepared.

Then one platinum loop each of *Acetobacter aceti subsp: xylinium* (ATCC 10821) grown at 30° C. for 3 days in a test tube slant agar medium (pH 6.0) having a composition of 0.5 g/dl of yeast extract, 0.3 g/dl of peptone and 2.5 g/dl of mannitol was inoculated on the culture solution followed by culturing at 30° C.

Culture was performed for 30 days under the conditions described whereby a gel-like membrane containing white bacterial cellulose polysaccharides was formed on the upper layer of the culture solution. This gel-like membrane of the cellulosic polysaccharides was washed with water to obtain bacterial cellulose.

The thus obtained bacterial cellulose was inserted between meal plates and press dried at 130° C. to obtain a bacterial cellulose sheet.

Physical properties of the bacterial cellulose sheet were measured by the oscillation lead method. The results shown in Table 18 were obtained.

TABLE 18

| Young's modulus | 13.6 GPa |
| Density | 1060 kg/m$^2$ |
| Resonance sharpness Q | 29.2 |
| Sonic velocity | 3580 m/sec. |

Then, paper honeycomb using the bacterial cellulose sheet as a skin agent was prepared. As a core, KCM 28 having a cell size of 3 mm, being immersed in 6% phenol and having a thickness of 2.8 mm was used.

A flat speaker of a 60 mm square was prepared using the obtained paper honeycomb as a diaphragm, which was designated Sample 1.

For purpose of comparison, paper honeycomb was prepared using the same core as Sample 1 and kraft paper as a skin agent. Using the paper honeycomb as a diaphragm, a flat speaker was prepared in a manner similar to Sample 1, which was designated Comparative Sample 1. The physical properties of kraft paper used herein are shown in Table 19.

TABLE 19

| Young's modulus | 2.4 GPa |
|---|---|
| Density | 565 kg/m² |
| Resonance sharpness Q | 35.1 |
| Sonic velocity | 2060 m/sec. |

Frequency characteristics of these Sample 1 and Comparative Sample 1 were measured. The results are shown in FIG. 3.

Figure 3:
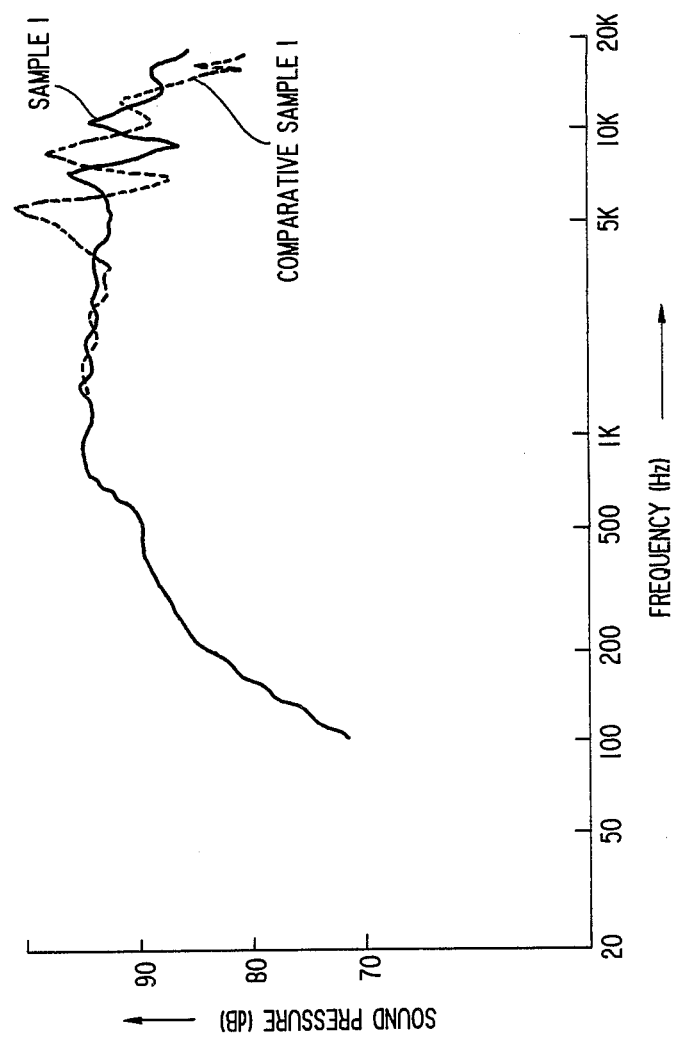
FIG. 3 is a frequency characteristic pattern of a flat speaker prepared using the bacterial cellulose as a skin agent, compared with a Comparative Sample.

From FIG. 3, it is noted that the high band reproducing threshold frequency is shifted to a high frequency band and at the same time, this peak becomes small in Sample 1 using the bacterial cellulose sheet as the skin agent and thus, the reproducing frequency band is greatly broadened.

EXAMPLE 19

The bacterial cellulose prepared in the foregoing example, was macerated using a macerator. After adding 4% (solid content ratio) of rosin size and 4% (solid content ratio) of aluminum sulfate as sizing agents, respectively, cone paper was prepared by a conventional paper making process. The physical properties of the obtained cone paper were measured by the oscillation lead method. The results shown in Table 20 were obtained.

TABLE 20

| Young's modulus | 6.3 GPa |
|---|---|
| Density | 982 kg/m² |
| Resonance sharpness Q | 21.0 |
| Sonic velocity | 2530 m/sec. |

Then, a full range speaker unit having a diameter of 12 cm was prepared by way of trial using this cone paper. This was designated Sample 2.

For comparison, a full range speaker unit was prepared in a manner similar to Sample 2, using cone paper prepared from ordinary kraft pulp, which was designated Comparative Sample 2. The physical properties of cone paper used herein are shown in Table 21.

TABLE 21

| Young's modulus | 2.5 GPa |
|---|---|
| Density | 620 kg/m² |
| Resonance sharpness Q | 21.0 |
| Sonic velocity | 2010 m/sec. |

The frequency characteristics of Sample 2 and Comparative Sample were measured. The results are shown in FIG. 4.

Figure 4:
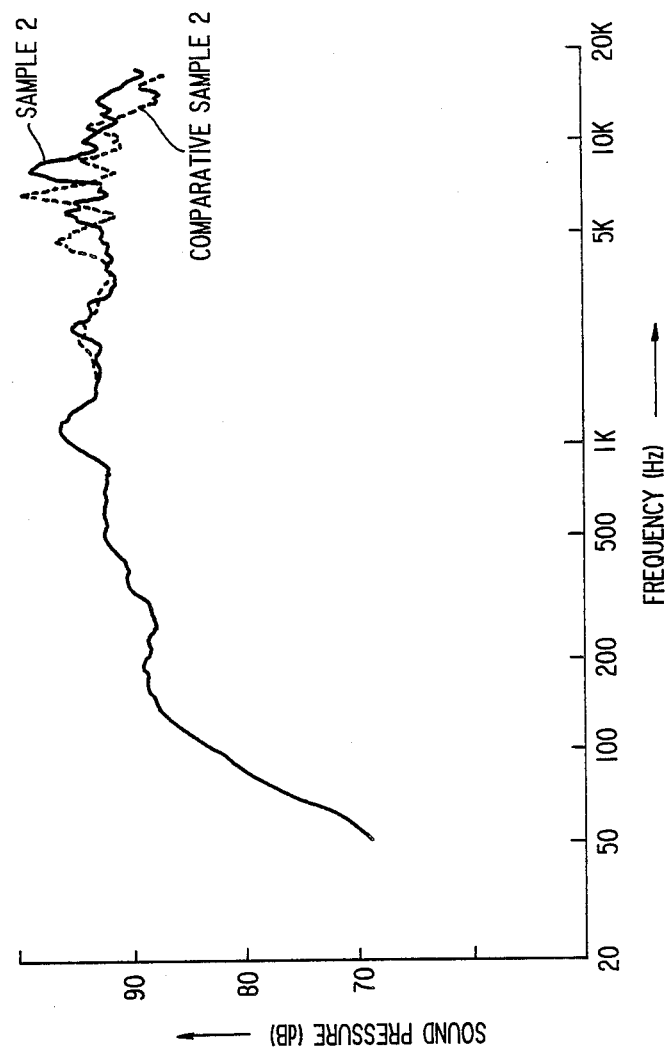
FIG. 4 is a frequency characteristic pattern of a cone type full range speaker prepared using cone paper subjected to paper making with bacterial cellulose, compared with a Comparative Sample.

From FIG. 4, it is noted that in Sample 2, prepared from cone paper using the bacterial cellulose, the high band reproducing threshold frequency was shifted to the high frequency band and the reproducing frequency band was broadened.

EXAMPLE 20

A portion of the wood pulp used for ordinary cone paper was replaced (5% and 15%) by the bacterial cellulose previously obtained in the foregoing example, as shown in Table 22 followed by paper making by the TAPPI method. Thus cone paper (Samples 3 and 4) was obtained. As wood pulp, N.U.SP (freeness, 570 ml, Csf) was used and as bacterial cellulose, a macerated (BC) was added. Further, cone paper obtained by paper making wood pulp alone was designated Comparative Sample 3.

The physical properties of these samples were measured by the oscillation lead method. The results are shown in Table 22.

TABLE 22

| | Young's Modulus GPa | Density kg/m² | Resonance Sharpness Q | Sonic Velocity m/sec |
|---|---|---|---|---|
| Sample 3 | 1.66 | 486 | 20.2 | 1790 |
| Sample 4 | 1.79 | 503 | 21.3 | 1880 |
| Comparative Sample 3 | 1.38 | 454 | 21.2 | 1750 |

From Table 22, it is noted that by incorporating the bacterial cellulose, improvement in the strength is obtained, while internal loss is maintained.

As is obvious from the foregoing description, in the acoustic diaphragm of the present invention, the bacterial cellulose is used, at least, as a portion of the cellulose fibers and therefore, a paper diaphragm having an extremely high strength is obtained and with a broadened reproducing frequency band.

Further, in the diaphragm of the present invention, there is no danger of problems arising such as a reduction of internal loss, a perception of incompatibility in sound quality, etc. as it is unnecessary to use non-cellulosic materials failing to form a hydrogen bond.

As noted, the molding material having a high dynamic strength of the present invention is excellent in tensile strength, expansion resistance, elasticity, etc. In particular, the sheet obtained after press squeezing and drying provides a sheet of an extremely high modulus of elasticity. In the articles of the examples, the modulus of elasticity was more than twice that of the sheet of polymetaphenyleneisophthalamide having the highest modulus of elasticity among secondary materials heretofore known.

Accordingly, the material can be used as reinforcing material for composite plastics requiring high strength, for example, as body materials such as ships, aircrafts, automobiles, etc., as plyboard base, etc., as high quality paper such as recording paper, etc., or as a diaphragm, etc. for percussion instruments.

Many modifications and variations of the present invention are possible in light of the above teachings. Therefore, it will be apparent to one of ordinary skill in the art that many changes and modifications can be made thereto without departing from the spirit or scope of the invention as set forth herein.

What is claimed as new and desired to be secured by Letters Patent of the United States is:

1. A molded material having high dynamic strength and a modulus of elasticity of at least 7.4 GPa, containing ribbon-shaped microfibrils of bacterial cellulose, which is produced by:
    (a) culturing a bacteria capable of producing cellulose in a nutrient medium,
    (b) withdrawing the cellulose produced from said culture in the form of a gel, and
    (c) pressing said gel to remove water from said cellulose by squeezing the same at a pressure sufficient to enhance said dynamic strength or macerating the same or a combination thereof.

2. The molded material having high dynamic strength according to claim 1, wherein said bacterial cellulose is produced by a microorganism belonging to the genus Acetobacter, the genus Pseudomonas or the genus Agrobacterium, or the bacteria *Sarcina ventriculi* and *Bacterium xylineides*.

3. The molded material having high dynamic strength according to claim 1, wherein a content of said bacterial cellulose is about 0.01% to 100%.

4. The molded material having high dynamic strength according to claim 1, which further contains at least one material selected from the group consisting of a hydrophilic high molecular weight material, a hydrophobic high molecular weight material, a metal and an inorganic material.

5. The molded material having high dynamic strength according to claim 1, which further contains a magnetic material.

6. The molded material having high dynamic strength according to claim 1, which further contains a material having electric conductivity.

7. The molded material having high dynamic strength according to claim 1, which further contains a material having high thermal conductivity.

8. The molded material having high dynamic strength according to claim 1, which contains a material having high resistance to weathering.

9. The molded material having high dynamic strength according to claim 1, which further contains a substance having high resistance to chemicals.

10. The molded material having high dynamic strength according to claim 1, wherein said bacterial cellulose is macerated.

11. The molded material having high dynamic strength according to claim 1, which process of preparation further comprises impregnating said molding material with an additive.

12. The molded material having high dynamic strength according to claim 1, which process of preparation further comprises coating said molding material with a water-proofing high-molecular weight material.

13. The molded material having high dynamic strength according to claim 1, which is molded into a sheet.

14. The molded material having high dynamic strength according to claim 13, wherein said sheet is paper.

15. The molded material having high dynamic strength according to claim 1, which is molded into a thread shape.

16. The molded material having high dynamic strength according to claim 15, which is molded into a cloth shape.

17. The molded material having high dynamic strength according to claim 1, which is molded into a solid form.

18. The molded material having high dynamic strength according to claim 1, wherein said molding material having high dynamic strength is an immobilized carrier having high dynamic strength.

19. The molded material having high dynamic strength according to claim 1, wherein said molding material having high dynamic strength is an acoustic diaphragm.

20. The molded material according to claim 1, wherein said ribbon-shaped microfibrils are approximately 100–500 Å in width and approximately 10–200 Å in thickness.

21. The molded material according to claim 1, wherein said bacterial cellulose comprises cellulose and one or more hetero polysaccharides having cellulose as a main chain and containing $\beta$-1,2 or $\beta$-1,3-glycans.

22. The molded material according to claim 21, wherein said hetero polysaccharide is selected from the group consisting of hexose, pentose, mannose, fructose, galactose, xylose, arabinose, ramnose and glucuronic acid.

23. The molded material according to claim 1, wherein said ribbon-shaped microfibrils are intertwined.

24. The molded material according to claim 1, wherein said bacterial cellulose has a modulus of elasticity in the range of about 10–20 GPa.

25. The molded material having high dynamic strength according to claim 1, wherein said gel is pressed in an orthogonal direction to remove said water.

26. The molded material having high dynamic strength according to claim 25, wherein a squeezing pressure of 1–10 kg/cm$^2$ is applied.

* * * * *